US012714749B2

(12) United States Patent
Hong et al.

(10) Patent No.: US 12,714,749 B2
(45) Date of Patent: Aug. 25, 2026

(54) ANTI-CK8 ANTIBODY AND EXOSOME COMPOSITIONS, METHODS OF MAKING, AND METHODS OF TREATING

(71) Applicants: Yu Wang, Dezhou City (CN); PEAK WAY GROUP INC., Tortola (VG)

(72) Inventors: Zihan Hong, Jiangyun City (CN); Weiliang Dai, Jiangyun City (CN)

(73) Assignees: Yu Wang, Dezhou City (CN); Peak Way Group Inc., Tortola (VG)

( * ) Notice: Subject to any disclaimer, the term of this patent is extended or adjusted under 35 U.S.C. 154(b) by 421 days.

(21) Appl. No.: 18/342,913

(22) Filed: Jun. 28, 2023

(65) Prior Publication Data

US 2023/0414751 A1 Dec. 28, 2023

(30) Foreign Application Priority Data

Jun. 28, 2022 (CN) ........................ 202210748445.2

(51) Int. Cl.

| | |
|---|---|
| ***A61K 39/395*** | (2006.01) |
| ***A61K 31/136*** | (2006.01) |
| ***A61K 31/167*** | (2006.01) |
| ***A61K 31/4745*** | (2006.01) |
| ***A61K 31/704*** | (2006.01) |
| ***A61K 39/00*** | (2006.01) |
| ***A61K 47/46*** | (2006.01) |
| ***A61P 35/00*** | (2006.01) |
| ***C07K 16/18*** | (2006.01) |

(52) U.S. Cl.
CPC ...... *A61K 39/39558* (2013.01); *A61K 31/136* (2013.01); *A61K 31/167* (2013.01); *A61K 31/4745* (2013.01); *A61K 31/704* (2013.01); *A61K 47/46* (2013.01); *A61P 35/00* (2018.01); *C07K 16/18* (2013.01); *A61K 2039/505* (2013.01); *C07K 2317/92* (2013.01)

(58) Field of Classification Search
None
See application file for complete search history.

(56) References Cited

FOREIGN PATENT DOCUMENTS

| | | | | |
|---|---|---|---|---|
| EP | 2020419 A1 * | 2/2009 | .............. | A61P 35/00 |
| WO | WO-2019164929 A1 * | 8/2019 | ......... | C07K 16/2803 |

* cited by examiner

*Primary Examiner* — Julie Wu
*Assistant Examiner* — Amy M. Chattin
(74) *Attorney, Agent, or Firm* — Bay State IP, LLC

(57) ABSTRACT

The present disclosure relates to a pharmaceutical composition containing an exosome and a preparation method thereof. The present disclosure provides a monoclonal antibody specifically targeting CK8, which can significantly improve the sensitivity of tumor cells. After being used together with the exosome loaded with a chemical drug, the monoclonal antibody of CK8 can effectively inhibit the propagation of tumors, and has good application prospect and application value.

7 Claims, 3 Drawing Sheets

Specification includes a Sequence Listing.

SEQUENCE LISTING

```
Sequence total quantity: 2
SEQ ID NO: 1           moltype = AA  length = 121
FEATURE                Location/Qualifiers
REGION                 1..121
                       note = Glu Val Gln Leu Val Glu Ser Gly Gly Gly Leu Val Gln
                        Pro Gly Gly Ser Leu Arg Leu Ser Cys Ala Ala Ser Gly Phe
                        Ser Leu Ser Ile Pro Tyr Ile Tyr Trp Val Arg Gln Ala Pro
                        Gly Lys Gly Leu Glu Trp Val Gly Ala Gln Gly Cys Gly Asn
                        Phe Tyr Leu Gly Trp Phe Gly Val Met
source                 1..121
                       mol_type = protein
                       organism = synthetic construct
SEQUENCE: 1
EVQLVESGGG LVQPGGSLRL SCAASGFSLS IPYIYWVRQA PGKGLEWVGA QGCGNFYLGW  60
FGVMSRFTIS KDNSKNTLYL QMNSLRAEDT AVYYCARFYG MVEIEHVEDV WGQGTLVTVS  120
S                                                                  121

SEQ ID NO: 2           moltype = AA  length = 111
FEATURE                Location/Qualifiers
REGION                 1..111
                       note = The amino acid sequence of the present application
                        is artificially synthesized
source                 1..111
                       mol_type = protein
                       organism = synthetic construct
SEQUENCE: 2
AYQMTQSPSS VSASVGDRVT ITCVQPKPHP MCRKWYQQKP GKAPKLLIYM QKDQDNGVPS  60
RFSGSGSGTD FTLTISSLQP EDFATYYCFF PRSRTVCDPK EFGGGTKVEI K           111
```

ANTI-CK8 ANTIBODY AND EXOSOME COMPOSITIONS, METHODS OF MAKING, AND METHODS OF TREATING

CROSS REFERENCE TO RELATED SEQUENCE LISTING

This application contains a computer readable form of a Sequence Listing, the name of the file being "Sequence_Listing", created on Jun. 28, 2023 and electronically submitted via Patent Center on Jun. 28, 2023. The size of the xml file is 4,000 bytes and the file is incorporated herein by reference.

CROSS REFERENCE TO RELATED APPLICATION

This application claims the benefit and takes priority of Chinese Patent Application No. 202210748445.2, filed on Jun. 28, 2022, the contents of which are herein incorporated by reference in its entirety as part of the present application.

TECHNICAL FIELD

The present disclosure relates to the field of biology, more particularly to a pharmaceutical composition containing an exosome and a preparation method thereof.

BACKGROUND

According to the latest data from world health organization, breast cancer has replaced lung cancer to become the world's largest tumor. About 420000 patients with breast cancer are increased in China each year, and the annual incidence rate has increased by 3%-4% in recent years. The progress of comprehensive treatment of breast cancer has played an important role, among which antibody drugs are important treatment means.

The most successful molecular targeting treatment of breast cancer is metastatic breast cancer drug trastuzumab (Herceptin®) targeting HER-2 overexpression. It is developed by Genentech®, a subsidiary of Roche®. It was approved by FDA in September 1998 to be used for treatment of HER-2 over-expressed metastatic breast cancers, and now has become a first-line drug. By administrating the drug, about ¼ patients with breast cancer are rescued and their lives are prolonged. In 2012, the sales volume in the world has reached 6.839 billion US dollars, ranking the eighth in the world's best-selling drugs. At the same time, Roche®, which developed Herceptin®, has established its dominant position in the research and development of HER-2 breast cancer antibody drugs. The neoadjuvant treatment of Trastuzumab has significant effect on breast cancer. A clinical trial showed that Trastuzumab combined with first-line chemotherapy drugs anthracycline, Cyclophosphamide or paclitaxel, compared with the same chemotherapy drugs alone, has better effect and improved survival rate, reducing the recurrence risk of patients by 46%-52% and the death risk by ⅓-53. This novel adjuvant therapy greatly improves the quality of life of patients. On Jun. 8, 2012, FDA approved it for the treatment of HER-2 positive metastatic breast cancer, which was developed by Genentech®, a subsidiary of Roche®. It is a monoclonal antibody for breast cancer after Trastuzumab and the first monoclonal antibody called HER dimerization inhibitor. A clinical trial combining Trastuzumab and Pertuzumab is under way. 808 patients with HER-2 positive metastatic breast cancer were randomly assigned. The control group received placebo+Trastuzumab+paclitaxel, while the Pertuzumab group received Pertuzumab+Trastuzumab+paclitaxel, to evaluate progression free survival and total survival. Compared with control group, the average progression free survival period of Pertuzumab group was extended from 12.4 months to 18.5 months. The results showed that the combination of Pertuzumab, Trastuzumab and paclitaxel as the first-line treatment for HER-2 positive metastatic breast cancer could significantly extend the progression free survival period without increasing the side effects on the heart. Other studies have shown that the combination of Bevacizumab and Pertuzumab is also better than the single drug. As a new target of breast cancer, HER-2 has won the favor of many scholars, who have taken it as the direction of drug development for breast cancer. Of course, it is also important to find a new target.

Endocrine therapy is one of the systemic treatments for breast cancer. Some endocrine therapy drugs can inhibit the reduction of estrogen synthesis and the combination with breast cancer cells, thus blocking the tumor signal transduction pathway to lead to the death of cancer cells, which plays an important role in reducing the risk of recurrence and death of breast cancer, and further prolonging the survival time of patients. However, such the drugs are easily metabolized, which is not conducive to their long-term effects.

Cytokeratin (CK) is the largest intermediate filament family, which is mainly distributed in epithelial cells and is a component of epithelial cytoskeleton. Normal epithelial cells of different types display specific CK markers, and research has confirmed that these cells still retain this labeling characteristic during tumor development. Therefore, CK is one of the epithelial biomarkers widely used in tumor research and pathological differential diagnosis. Current research shows that inhibiting the activity of CK8 can inhibit the activity of cancer cells, which can be used for cancer treatment.

In recent years, researches on exosome delivery drugs have been gradually increased, and some small molecule chemical drugs and genetic drugs have been successfully loaded into exosomes. The exosomes combine the advantages of cell and nanotechnology in drug delivery: compared with Cell therapy, the exosomes are easier to store and have higher safety. For example exosome delivery gene drugs do not deposit in different parts of the body, leading to immune rejection. In addition, the exosomes can also be separated from patient fluids and modified to move back to the same patient, greatly reducing the possibility of immune reactions in clinical practice; the exosome delivery drugs can improve the stability of drugs. For example, the exosomes can protect nucleic acids from ribozyme hydrolysis during transportation. At the same time, the exosomes can directly enter the cell fluid to avoid metabolic elimination, thereby prolonging the circulation time of drugs in the body; the exosomes are nanoscale molecules that carry cell surface substances, thus possessing strong ability to penetrate various biological barriers; the exosomes have a natural targeting ability based on donor cells. For example, the exosomes derived from tumor cells carry tumor specific antigens, proteins, and RNA, which can play an anti-tumor immune role.

At present, therapeutic means for treating breast cancer with an exosome loaded drug are not rich enough, without enough alternative ways, which is worth further researching.

SUMMARY

The present disclosure overcomes the defects of the prior art and provides a drug that can effectively improve the drug sensitivity in the treatment of breast cancer.

In one aspect, provided is a monoclonal antibody specifically binding to CK8, which can improve the drug sensitivity of the cancer cells.

Further, the monoclonal antibody of CK8 of the present disclosure is a CK8-1R5 monoclonal antibody, and the light chain variable region sequence and the heavy chain variable region sequence of the antibody are as follows:

the amino acid sequence of the heavy chain variable region is shown in SEQ ID NO: 1, and is

EVQLVESGGGLVQPGGSLRLSCAASGFSLSIPYIYWVRQAPGKGLEW

VGAQGCGNFYLGWFGVMSRFTISKDNSKNTLYLQMNSLRAEDTAVYY

CARFYGMVEIEHVEDVWGQGTLVTVSS

The amino acid sequence of the light chain variable region is shown in SEQ ID NO: 2, and is

AYQMTQSPSSVSASVGDRVTITCVQPKPHPMCRKWYQQKPGKAPKLLI

YMQKDQDNGVPSRFSGSGSGTDFTLTISSLQPEDFATYYCFFPRSRTV

CDPKEFGGGTKVEIK.

The amino acid sequence of CDR-H1 (in this specification, CDR-H1 represents heavy chain CDR1) is shown in IPYIY;

The amino acid sequence of CDR-H2 (in this specification, CDR-H2 represents heavy chain CDR2) is shown in AQGCGNFYLGWFGVMS;

The amino acid sequence of CDR-H3 (in this specification, CDR-H3 represents heavy chain CDR3) is shown in FYGMVEIEHVEDV;

The amino acid sequence of CDR-L1 (in this specification, CDR-L1 represents heavy chain CDR1) is shown in VQPKPHPMCRK;

The amino acid sequence of CDR-L2 (in this specification, CDR-L2 represents heavy chain CDR2) is shown in MQKDQDN;

The amino acid sequence of CDR-L3 (in this specification, CDR-L3 represents heavy chain CDR3) is shown in FFPRSRTVCDPKE.

Further, the present disclosure provides use of a monoclonal antibody CK8-1R5 in preparing a drug for treating breast cancer, wherein the monoclonal antibody CK8-1R5 of CK8 improves the drug sensitivity of drug-resistant breast cancer cells.

Further, the present disclosure provides use of a monoclonal antibody CK8-1R5 of CK8 and an exosome loaded with a chemical anticancer drug in preparing a drug for treating breast cancer, wherein the monoclonal antibody CK8-1R5 of CK8 improves the drug sensitivity of drug-resistant breast cancer cells.

further, the exosome is isolated from tumor cell culture supernatant, the loading is that a chemical anticancer drug loaded exosome is prepared by mixing an equal amount of exosome with a chemical anticancer drug through electroconversion under electric shock conditions of a 400V voltage, a 125 μF capacitance and a 4 mm electroconversion cup, subsequently free and non-specific binding chemical anticancer drugs are removed by filtration with an inverted centrifugal ultrafiltration membrane.

Further, the anticancer drug of the present disclosure is mitoxantrone, topotecan or daunorubicin.

Further, the present disclosure provides use of a monoclonal antibody CK8-1R5 of CK8 and a BCRP inhibitor in preparing a drug for treating breast cancer, wherein the monoclonal antibody CK8-1R5 of CK8 and the BCRP inhibitor improve the drug sensitivity of drug-resistant breast cancer cells.

Further, the drug of the present disclosure further comprises mitoxantrone, topotecan or daunorubicin.

Further, the present disclosure provides use of a monoclonal antibody CK8-1R5 of CK8 and an exosome loaded with a chemical anticancer drug in preparing a drug for treating breast cancer, wherein the monoclonal antibody CK8-1R5 of CK8 improves the drug sensitivity of drug-resistant breast cancer cells.

Further, the exosome is isolated from culture supernatant of tumor cells, the loading is that a chemical anticancer drug loaded exosome is prepared by mixing an equal amount of exosome with a chemical anticancer drug through electroconversion under electric shock conditions of a 400V voltage, a 125 μF capacitance, and a 4 mm electroconversion cup, subsequently, free and non-specific binding chemical anticancer drugs are removed by filtration with an inverted centrifugal ultrafiltration membrane.

Further, the anticancer drug of the present disclosure is mitoxantrone, topotecan or daunorubicin.

Further, the BCRP inhibitor is KS176 whose structure is shown in Formula 1:

(Formula 1)

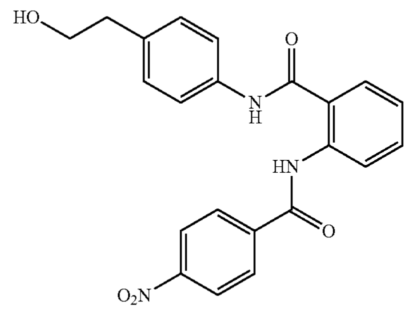

Further, the drug of the present disclosure also comprises a pharmaceutically acceptable carrier.

In some embodiments, a pharmaceutical composition can comprise one or more drug excipients or carriers. "drug excipients or carriers" can be any suitable components (for example applicable to drugs, for drug dosage, for drug release timing, for this disease, for disease state, or for delivery route), including but not limited to water (such as boiled water, distilled water, filtered water, water without pyrogen, or water containing chloroform), sugar (such as sucrose, glucose, mannitol, sorbitol, xylitol or syrup prepared therefrom), ethanol, glycerol, diol (such as propylene glycol), acetone, ether, dimethylsulfoxide (DMSO), surfactants (such as ethanol, glycerol, diol, acetone, ether, DMSO). Anionic surfactants, cationic surfactants, zwitterion surfactants, or non-ionic surfactants (such as polysorbate), oil (such as animal oil, vegetable oil (such as coconut oil or peanut oil) or mineral oil), oil derivatives (such as ethyl oleate, glycerol monostearate or hydrogenated glyceride), excipients, preservatives (such as cysteine, methionine, antioxidants (such as vitamins (such as A, E or C), selenium, retinyl palmitate, sodium citrate, citric acid, chloroform or paraben (such as methyl 4-hydroxybenzoate or propyl 4-hydroxybenzoate), or combinations thereof In some embodiments, the pharmaceutical composition can be present in a dosage form suitable for local, subcutaneous, intrathecal, intraperitoneal, oral, parenteral, rectal, skin, and nasal pathways. In other embodiments, the pharmaceutical composition can be present in a dosage form suitable for parenteral, mucosal, intravenous, subcutaneous, local, intradermal, oral, sublingual, intranasal or intramuscular administration. The pharmaceutical composition can be, for example, a tablet, a capsule, a pill, a powder, a granule, a suspension, an emulsion, a solution, gel (including hydrogel), a paste, a salve, a cream, an electuary, a filling agent, a delivery device, a suppository, an enema, an injection, an implant, a spray, an aerosol or other suitable forms.

In addition, the pharmaceutical composition of the present disclosure can also comprise other pharmaceutical reagents, carriers, adjuvants, diluents, and excipients. In certain embodiments, the carriers, excipients or excipients can promote the administration and delivery of the composition, and/or improve the preservation of the composition. In other embodiments, the one or more carriers include but are not limited to saline solutions, such as physiological saline, Ringer's solution, PBS (phosphate buffered saline), and general mixtures of various salts, including potassium salts and phosphate, with or without sugar additives such as glucose. The carrier may include both aqueous and non-aqueous sterile injection solutions, which may include anti-oxidants, buffering agents, antibacterial agents, antibacterial antibiotics, and solutes that make the formulation isotonic with the intended recipient's body fluids; and water-based and non-water-based sterile suspensions, which can include suspensions and thickeners. In other embodiments, the one or more excipients may include but are not limited to water, saline, glucose, glycerol, ethanol, and combinations thereof. Non-toxic auxiliary substances such as wetting agents, buffering agents, or emulsifiers can also be added into the composition. Oral preparations may include commonly used excipients, such as pharmaceutical grade mannitol, lactose, starch, magnesium stearate, saccharin sodium, cellulose and magnesium carbonate.

Beneficial Effects

The present disclosure provides a monoclonal antibody specifically targeting CK8, which can significantly enhance the drug sensitivity of tumor cells. After being used with the exosome loaded with the chemical drug, the monoclonal antibody of CK8 can effectively inhibit tumor proliferation and has good application prospects and value.

DETAILED DESCRIPTION OF THE EMBODIMENTS

In order to provide a clearer explanation of the specific embodiments of the present disclosure or the technical solutions in the prior art, a brief introduction will be given to the accompanying drawings required for the specific embodiments or the description of the prior art. It is evident that the accompanying drawings in the following description are some embodiments of the present disclosure. For ordinary technical personnel in the art, other accompanying drawings can be obtained based on these drawings without any creative effort.

Example 1 Preparation of Human CK8 Protein

According to the gene sequence of human CK8, upstream and downstream primers were designed, wherein:

```
upstream primer:
5'-CGGAATTCATGTCCATCAGGGT-3'
(EcoR I restriction site);

downstream primer:
5'-GTCGACTCACTTGGGCAGGAC-3'
(Sal/I restriction site);
```

A human breast cancer cell line MCF7 was activated and cultured, RNA was extracted, cDNA was reversely transcripted, and the above primers were used for PCR. The PCR cycle parameters were as follows: pre-denature at 94° C. for 10 min, denature at 94° C. for 45 s, anneal at 62° C. for 45 s, extend at 72° C. for 2 min, for 30 cycles in total, and finally extend at 72° C. for 10 min. The PCR product was recovered by agarose gel electrophoresis and ligated with a T vector, and DH5a competent cells were transformed. After screening and identification of positive clones, plasmids were extracted and doubly digested with restriction endonuclease EcoRI and SalI. Purification, recovery and quantification were performed using a target gene fragment gel recovery kit. The expression vector Pet-28a (+) subjected to double digestion via EcoRI and SalI was ligated with a T4DNA ligase, and competent BL21 (DE3) strains prepared by a calcium chloride method were transformed. Via identification, recombinant colonies were picked for amplified cultivation.

Figure 1:
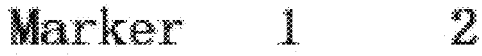
FIG. 1 is a sodium dodecyl sulfate polyacrylamide gel electrophoresis (SDS-PAGE) graph of recombinant protein CK8 expression.
Figure 1:
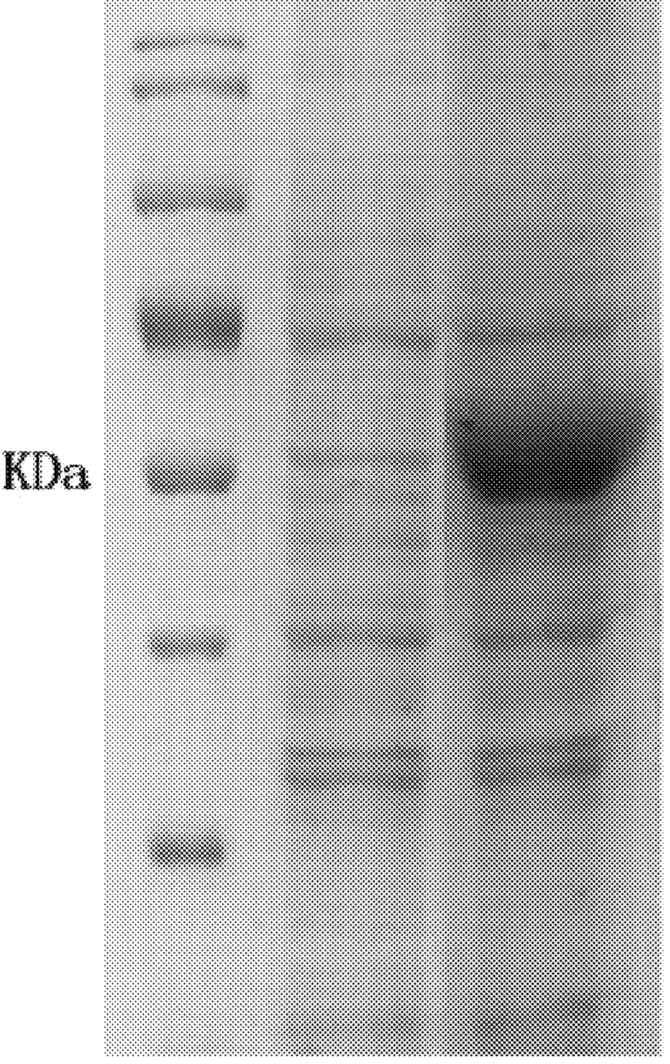

A single colony was picked and resuscitated overnight in an LB solution containing kanamycin, then inoculated with the same culture medium at a ratio of 1:100. When aerated culture at 37° C. until the A600 value was about 0.6, human IPTG was added so that a final concentration was 1 mmol/L, thallus were broken after induction for 1 h, 3 h and 5 h at 30° C., 10 μl of broken thallus was subjected to SDS-PAGE. The results are shown in FIG. 1, and the level of the protein expressed at 5 h is the highest. The bacterial solution induced for 5 h was centrifuged and then underwent protein purification using Ni column for later use.

The results are shown in FIG. 1. After induction for 5 hours, it can be clearly seen that the target band staining is clear at Mr58 000 in Lane 2. Lane 1 is blank strain control, from which can be seen that there is no target band expression, indicating that the expression level of recombinant protein CK8 expressed in this study is very good.

Example 2 Preparation of Human CK8 Protein Monoclonal Antibody and its Performance Testing 100 μg of purified recombinant CK8 protein and 10 μg of CpG were mixed, the obtained mixture was ultrasonically emulsified with an equal amount of Freund's incomplete adjuvant and then intramuscularly injected onto hips at two sides of BALB/c mouse, a total of 3 mice were immunized, once on day 0, 14 and 28 respectively. 7-10 d after the third immunization, several drops of mouse tail vein blood were taken and serum was isolated. When the antibody titer measured by indirect immunofluorescence assay (IFA) reaches 1:5000 or above, the mice with the highest titer were selected, immunity was strengthened once, and cell fusion test was performed after 3 d. The splenic lymphocyte suspension was prepared from the spleen of aseptic immunized mice. It was mixed with SP2/0 myeloma cells in a 1:10 quantity ratio. After low-speed centrifugation, the supernatant was discarded, and the preheated fusion promoter (50% PEG4000) was slowly added to the precipitation. The volume of HAT selected medium (containing 20% Fetal bovine serum) constant volume cell suspension was 50 ml. The cell suspension was transferred to a 96-well cell culture plate (100 μL/well) for 3 weeks, and cell clones were picked and inoculated to a 24-well plate for further cultivation. The supernatant of 24-well plate cultured cells was used as a primary antibody and purified CK8 protein as a coating antigen, and positive clones secreting antibodies against CK8 protein were screened by using indirect ELISA. The positive clones obtained through screening were subcloned for three times after limited dilution with HA selective medium, and screened by the same method until the positive rate of all cell culture wells was 100%. It was confirmed that a hybridoma cell line stably secreting anti-CK8 protein monoclonal antibody was obtained, one of which was CK8-1R5. The obtained cell line was subjected to amplified cultivation, and the culture supernatant which contains a large amount of monoclonal antibody CK8-1R5 was collected.

The titer of monoclonal antibodies was determined using an indirect ELISA method. An ELIASA plate (100 μl/well) was coated with 10 ml of purified recombinant CK8 protein overnight at 4° C., and sealed for 1 h at 10% BSA room temperature. Different concentrations of CK8-1R5 monoclonal antibodies subjected to multiple dilution were added respectively, and incubated at 37° C. for 1 h. After washing 3 times with 0.05% PBST, HRP labeled sheep anti-mouse IgG with a dilution of 1:2000 was added, and the obtained mixture was incubated at 37° C. for 1 h and then washed. A developing agent ABTS was added, and the absorbance (A) value at a wavelength of 405 nm was read on microplate reader. Simultaneously, SP2/0 myeloma cell culture supernatant was used as negative control. The highest dilution ratio of the sample that produces a positive reaction was used as its potency. The results are seen in Table 1.

TABLE 1

Titer of monoclonal antibody CK8-1R5

| Monoclonal antibody | 1:400 | 1:800 | 1:1600 | 1:3200 | 1:6400 | Control |
|---|---|---|---|---|---|---|
| CK8-1R5 | 1.679 | 1.136 | 0.821 | 0.596 | 0.284 | 0.056 |

It can be seen from the results in Table 1 that the potency of the monoclonal antibody CK8-1R5 is 1:6400, with a good effect.

The purified recombinant CK8 protein was used to coat the ELISA plate, the CK8-1R5 monoclonal antibody diluted at 1:500 was used as a primary antibody (mouse derived), and various types (IgG, IgM, IgA) of HRP-labeled sheep anti-mouse antibodies were used as a secondary antibody. After conventional incubation and washing the plate, a human developing agent was added, and the absorbance (A) value at 405 nm wavelength was read on the microplate reader to identify the classes and subclasses of mAbs. The results are shown in FIG. 2.

Figure 2:
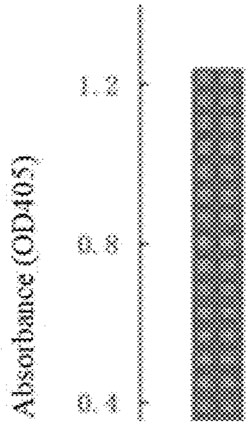
FIG. 2 is a subtype identification result graph of a monoclonal antibody.

It can be seen from the results of FIG. 2 that the CK8-1R5 monoclonal antibody is IgG, specifically IgG1.

Specificity identification: each 1 μg of CK8 protein, MCF7 cell lysate, BSA, Escherichia coli lysate and mouse fibroblast NIH3T3 lysate was used to coat the ELISA plate, with PBS wells as blank control. After washing with PBS, 2.5% skimmed milk was added and the plate was sealed at room temperature for 1 h. After washing with PBS, 1:10 diluted cell culture supernatant (monoclonal antibody, primary antibody) was added, the plate was incubated at 37° C. for 1 and washed with 0.05% PBST 3 times, 1:2000 diluted HRP labeled sheep anti-mouse IgG (second antibody) was added, washed after incubation at 37° C. for 1 h, a developing agent ABTS was added, and the absorbance (A) value at 405 nm wavelength was read on the microplate reader. The results are shown in FIG. 3.

Figure 3:
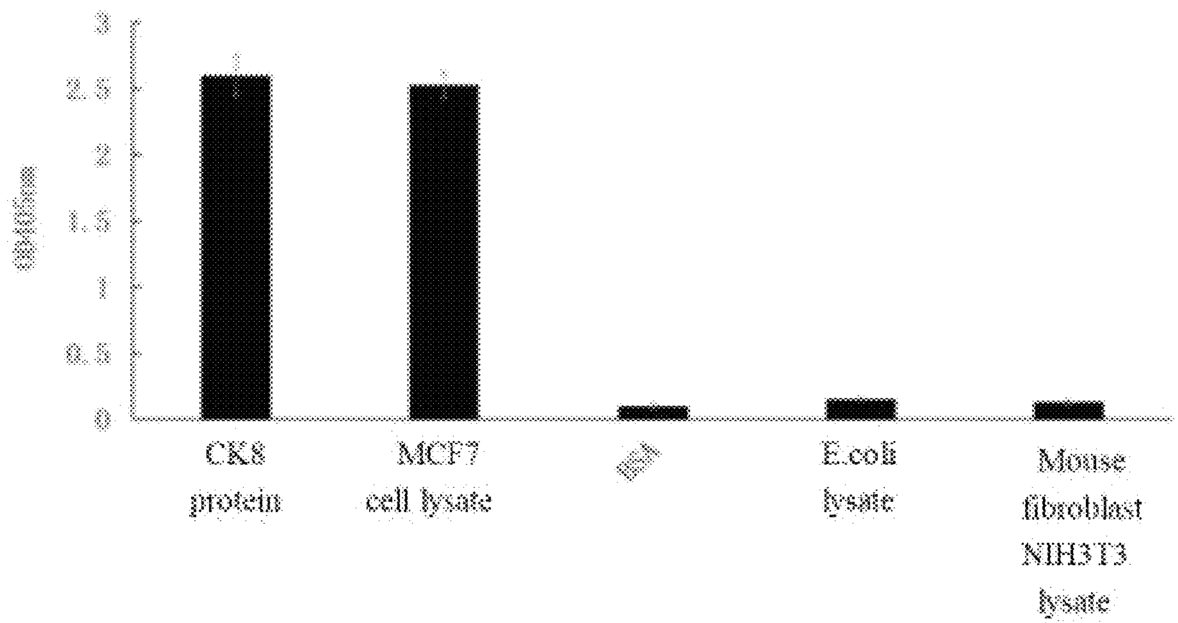
FIG. 3 is a specificity identification result graph of a monoclonal antibody.

It can be seen from the results in FIG. 3 that the CK8-1R5 monoclonal antibody of the present disclosure only binds to CK8 protein or MCF7 cell lysate expressing the CK8 protein, and does not bind to other samples, demonstrating good specificity.

Binding ability test: 1 mg of CK8-1R5 monoclonal antibody was taken and dispersed into 1 mL of PBS buffer solution; the prepared antibody dispersion was immobilized on an aminopropyl sensor, the sensor immobilized with the antibody was balanced in PBS buffer and then interact with different concentrations of CK8 protein solutions respectively, and then the spectral phase difference caused by CK8 protein binding to the antibody was recorded. After binding equilibrium, the sensor was placed in PBS buffer, the spectral phase difference caused by protein dissociation from the antibody was recorded, and the antibody's affinity to the protein was fit based on the phase difference. The experimental results show that the affinity of the prepared antibody for CK8 protein is $6.33\times10^{-9}$M, with excellent binding ability.

Meanwhile, light and heavy chain amplification primers were used for amplification and sequencing to obtain the light chain variable region sequence, as shown in SEQ ID NO: 1, of the CK8-1R5 monoclonal antibody, and the heavy chain variable region sequence, as shown in SEQ ID NO: 2, of the CK8-1R5 monoclonal antibody

Example 3 Efficacy Evaluation of Monoclonal Antibody CK8-1R5

The SRB method was used to detect the sensitivity of cells to chemotherapy drugs: 800 μg/L mitoxantrone was added in the process of culturing MCF-7/MX cells to maintain drug resistance, and the drug administration stopped two weeks before experiment. 100 μg/mL CK8-1R5 monoclonal antibody and/or 100 μg/mL BCRP inhibitor KS176 (Bai Olette, product No.: M01428) were added into cell culture wells of MCF-7/MX cells, and the culture medium was added for blank control. After 24 hours of culture, digestive cells were inoculated into a 96-well plate, with 2000 cells/well, and 3 double wells. The cells were continued to be cultured for 24 h until complete adherence. After adding different concentrations of chemotherapy drugs (mitoxantrone, topotecan, and daunorubicin) to act for 48 h, the culture was terminated. 50 IA of pre-cooled 50% (mass/volume) trichloroacetic acid was added into each well for immobilizing cells, and the culture plate was transferred into a refrigerator at 4° C. after standing for 1 h; the culture plate was taken, each well was washed with deionized water 5 times to remove TCA, and then dried in air; after complete drying, 100 μl of 0.4% SRB prepared with 1% acetic acid was added into each well and stained for 30 min at room temperature, and then the solution in each well was discarded; the well was washed 5 times using 1% acetic acid to remove unbound dye, and dried in air; 150 μl of 10 mM Tris alkaline solution with pH 10.5 was used for dissolving the sample in each well, the sample was oscillated for 5 min on a flat oscillator, and the absorbance of each well at 490 nm was measured on a BioRad microplate reader. The IC50 value was calculated using Prism software. The results are seen in Table 1.

TABLE 1

The sensitivity of inhibitor in each group on MCF-7/MX cells and chemotherapy drugs

| Each group | Mitoxantrone (IC50, nM) | Topotecan (IC50, nM) | Daunorubicin (IC50, nM) |
|---|---|---|---|
| MCF-7/MX | 24963 ± 1346 | 17965 ± 1342 | 431.19 ± 10.23 |
| MCF-7/MX + 100 μg/mL CK8-1R5 monoclonal | 9672 ± 637* | 8024 ± 659* | 142.71 ± 12.42* |
| MCF-7/MX + 100 μg/mL KS176 | 6754 ± 443* | 6123 ± 501* | 131.50 ± 15.32* |
| MCF-7/MX + 100 μg/mL CK8-1R5 monoclonal antibody + 100 μg/mL KS176 | 3214 ± 345* | 3402 ± 296* | 105.41 ± 9.65* |

*represents that compared with a group without drug, there is significant difference $P < 0.05$.

It can be seen from Table 1 that after the CK8 monoclonal antibody and the BCRP inhibitor are added into MCF-7/MX cells, the sensitivities of chemotherapeutic drugs mitoxantrone, topotecan, daunorubicin are simultaneously improved, and the drug resistance phenotype is significantly reversed. Conclusion: The combined use of CK8 and the BCRP inhibitor can significantly treat multidrug resistance in MCF-7/MX, and has a good therapeutic effect.

Example 4 Preparation of Exosome Loaded Drugs and Experimental Treatment with CK8-1R5 Monoclonal Antibody MCF-7 was selected as a source cell of a tumor exosome, and the culture medium was DMEM with 10% Fetal bovine serum. After being transferred to a cell incubator (37° C. constant temperature, volume fraction, 5% $CO_2$) for 48 h, the supernatant of tumor cells was collected and gradient centrifuged (2000×g, centrifuge, 20 min, 10000×g, centrifuge for 30 min) to remove cell debris, large vesicles were removed using a 0.22 μm filter; the filtrate was centrifuged for 70 min at 100000×g, the supernatant was discarded and then resuspended with 100 μL of DPBS at the bottom of a centrifuge tube, and the exosomes were recovered and stored at 80° C. in refrigerator for future use.

An equal amount of exosomes was mixed with daunorubicin, and the daunorubicin loaded exosome was prepared by electroporation under electric shock conditions of a 400V voltage, a 125 μF capacitance and a 4 mm electric rotary cup. Subsequently, free and non-specific binding daunorubicin was removed by filtration with an inverted centrifugal ultrafiltration membrane.

After the inguinal areas of mice were subcutaneously inoculated with $5\times10^5$ MCF7/MX cells for 7 d, tumor bearing mice were randomly divided into 5 groups according to random number table: blank control group, exosome group loaded with erythromycin, exosome group loaded with CK8-1R5 monoclonal antibody combined with erythromycin, CK8-1R5 monoclonal antibody group, and erythromycin group. Each treatment group was subcutaneously injected through tail veins according to the above grouping (50 μg/pieces), wherein the blank control was administrated with a 100 μl normal saline solution; in the exosome group loaded with CK8-1R5 monoclonal antibody combined with erythromycin, the monoclonal antibody was administrated 50 μg/pieces, after 24 h, the exosome was administrated 50 μg/pieces. Each of other groups was administrated 100 μg/pieces. After 7d, administration was performed once again. After 14 days of the first administration, the mice were euthanized and the tumor volume=short diameter$^2$× Long diameter/2 was measured×Long diameter/2. The results are shown in FIG. 4.

Figure 4:
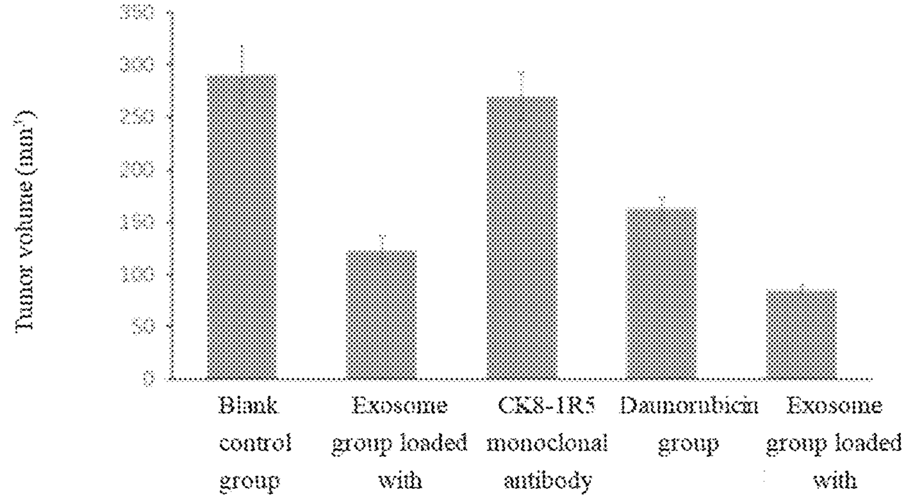
FIG. 4 is a result graph showing treatment of combination of an exosome loaded drug with a monoclonal antibody on growth of tumor.

It can be seen from the results in FIG. 4 that after 14 days of administration, there is a statistically significant difference ($P<0.05$) between treatment groups containing daunorubicin and blank control group. However, there is no statistically significant difference ($P>0.05$) between single monoclonal antibody treatment group and blank control group, indicating that the inhibitory effect of the single monoclonal antibody on cells is relatively small. The tumor volume of the CK8-1R5 monoclonal antibody combined with exosome group loaded with daunorubicin was only (85.1±5.2) $mm^3$. The treatment effect of the exosome group loaded with daunorubicin is far better than that of the group without monoclonal antibody, which indicates that CK8-1R5 monoclonal antibody can significantly reduce the drug resistance of cancer cells, thus improving the treatment effect.

It should be understood that the present disclosure is not necessarily limited to the details of the construction and arrangement of the components described in the following description and/or illustrated in the accompanying drawings in its application. The present disclosure can have embodiments other than those described and practiced or carried out in different ways. Moreover, it should be understood that the phrases and terminology used in this article, as well as the abstract, are for descriptive purposes and should not be considered restrictive

What is claimed is:

1. A monoclonal antibody that binds CK8 antigen, wherein the antibody is CK8-1R5 which comprises (i) a heavy chain variable region of SEQ ID NO: 1 and (ii) a light chain variable region of SED IQ NO: 2.

2. A method of treating breast cancer comprising administering the monoclonal antibody of claim 1, wherein the monoclonal antibody improves drug sensitivity of drug-resistant breast cancer cells.

3. A method of treating breast cancer comprising administering (i) the monoclonal antibody of claim 1 and (ii) an exosome loaded with one or more chemical drugs, wherein the monoclonal antibody improves drug sensitivity of drug-resistant breast cancer cells.

4. The method of treating breast cancer of claim 3, wherein:

(1) the exosome is an exosome isolated from culture supernatant of breast cancer cells;

(2) the exosome is loaded by mixing an equal amount by weight of exosome with chemical drugs through electroconversion, wherein (i) the chemical drugs are anticancer drugs and (ii) electroconversion comprises 400V, a 125 μF capacitance and a 4 mm electroconversion cup; and (3) free and non-specifically bound chemical anticancer drugs are removed by filtration with an inverted centrifugal ultrafiltration membrane.

5. The method of treating breast cancer of claim 4, wherein the anticancer drug is mitoxantrone, toptecan or daunorubicin.

6. A method of treating breast cancer comprising administering (i) the monoclonal antibody of claim 1 and (ii) a breast cancer resistance protein (BCRP) inhibitor is administered to treat breast cancer, wherein the monoclonal antibody and the BCRP inhibitor combination therapy improves drug sensitivity of the drug-resistant breast cancer cells.

7. The method of treating breast cancer of claim 6, wherein the drug is mitoxantrone, toptecan or daunorubicin.

* * * * *